(12) United States Patent
Brenowitz et al.

(10) Patent No.: US 9,279,814 B2
(45) Date of Patent: Mar. 8, 2016

(54) SOLID STATE SYNTHESIS HYDROXYL RADICALS FOR HIGH THROUGHPUT STRUCTURE DETERMINATION OF PROTEINS AND NUCLEIC ACIDS BY OXIDATIVE FOOTPRINTING

(75) Inventors: Michael Brenowitz, Chappaqua, NY (US); Jorg Schlatterer, Bronx, NY (US)

(73) Assignee: Albert Einstein College of Medicine, Inc., Bronx, NY (US)

( * ) Notice: Subject to any disclaimer, the term of this patent is extended or adjusted under 35 U.S.C. 154(b) by 1394 days.

(21) Appl. No.: 13/063,833

(22) PCT Filed: Aug. 24, 2009

(86) PCT No.: PCT/US2009/004804
§ 371 (c)(1),
(2), (4) Date: Apr. 8, 2011

(87) PCT Pub. No.: WO2010/030321
PCT Pub. Date: Mar. 18, 2010

(65) Prior Publication Data
US 2011/0207616 A1    Aug. 25, 2011

Related U.S. Application Data

(60) Provisional application No. 61/192,097, filed on Sep. 15, 2008.

(51) Int. Cl.
*G01N 33/68* (2006.01)
*B01L 3/00* (2006.01)
*C07H 21/00* (2006.01)

(52) U.S. Cl.
CPC ............. *G01N 33/68* (2013.01); *B01L 3/5027* (2013.01); *C07H 21/00* (2013.01); *C12Q 2523/107* (2013.01); *C12Q 2565/125* (2013.01); *C12Q 2565/627* (2013.01); *G01N 33/6848* (2013.01); *Y10T 436/143333* (2015.01)

(58) Field of Classification Search
CPC .. G01N 33/68; G01N 33/6848; B01L 3/5027; C12Q 2565/627; C12Q 2565/125; C12Q 2523/107; C07H 21/00; Y10T 436/143333
See application file for complete search history.

(56) References Cited

U.S. PATENT DOCUMENTS

| 6,117,634 A | 9/2000 | Langmore et al. |
| 6,165,726 A | 12/2000 | Iyyalasomayazula |
| 6,762,022 B2 | 7/2004 | Makarov et al. |

FOREIGN PATENT DOCUMENTS

WO    WO 2008/073175    6/2008

OTHER PUBLICATIONS

Guan et al. (Trends in Biochemical Sciences, Oct. 2005, vol. 30 No. 10).*

(Continued)

*Primary Examiner* — Jeremy C Flinders
(74) *Attorney, Agent, or Firm* — Amster, Rothstein & Ebenstein LLP

(57) ABSTRACT

The present invention generally relates to an apparatus for structural mapping of a macromolecule comprising an amount of persulfide effective to generate hydroxyl radicals upon contact with an aqueous solution. The present invention further relates to methods for structural mapping a macromolecule in an aqueous solution and methods for structural mapping a plurality of macromolecules in parallel, wherein each macromolecule is in a separate aqueous solution.

7 Claims, 6 Drawing Sheets

(56) References Cited

OTHER PUBLICATIONS

Cohn et al. (Geochemical Transactions, 2006, vol. 7:3 pp. 1-11).*
Biswas, et al., Mapping RNA-Protein Interactions in Ribonuclease P from *Escherichia coli* using Disulfide-linked EDTA-Fe, J. Mol. Biol. (2000) 296, 19-31.
Schlatterer, et al, Complementing global measures of RNA folding with local reports of backbone solvent accessibility by time resolved hydroxyl radical footprinting, Methods, Oct. 2009; 49(2): 142-147.
Written Opinion of the International Searching Authority dated Nov. 4, 2009 in connection with PCT/US09/04804.
International Search Report issued Nov. 4, 2009 in connection with PCT/US09/04804.

* cited by examiner

SOLID STATE SYNTHESIS HYDROXYL RADICALS FOR HIGH THROUGHPUT STRUCTURE DETERMINATION OF PROTEINS AND NUCLEIC ACIDS BY OXIDATIVE FOOTPRINTING

CROSS-REFERENCE TO RELATED APPLICATIONS

This application is a U.S. national stage entry under 35 U.S.C. §371 of PCT International Patent Application No. PCT/US2009/004804, filed Aug. 24, 2009, and claims priority to U.S. Provisional Patent Application No. 61/192,097, filed Sep. 15, 2008, the contents of which are incorporated herein by reference in their entirety.

STATEMENT OF GOVERNMENT SUPPORT

This invention was made with government support under Grant No. PO1-GM066275 awarded by the National Institutes of Health. The government has certain rights in the invention.

FIELD OF THE INVENTION

The present invention generally relates to an apparatus for structural mapping of a macromolecule comprising an amount of persulfide effective to generate hydroxyl radicals upon contact with an aqueous solution and related methods.

BACKGROUND OF THE INVENTION

Throughout this application various publications are referred to by Arabic numerals in brackets. Full citations for these references may be found at the end of the specification immediately preceding the claims. The disclosures of these publications are hereby incorporated by reference in their entireties into the subject application to more fully describe the art to which the subject application pertains.

Structural mapping or 'footprinting' refers to methods in which the surface of nucleic acids and proteins accessible to the solvent is mapped with as fine as single residue resolution. Footprinting assays can be viewed as a collection of 'molecular cameras' that snap pictures of the position of each residue. Footprinting assays examine structure, ligand binding and/or conformational changes by determining the accessibility of the backbone or residues of macromolecules through their sensitivity to chemical or enzymatic modification or cleavage (reviewed by [3, 4]). The key characteristics of a footprinting assay are that i) the reaction of the footprinting probe with the polymer is limited such that each position along the chain is sampled with equal probability, and ii) cleavage or modification products are uniquely identified (FIG. 1).

The ability of proteins to undergo association and folding reactions has long been known to be a fundamental feature of cellular function across all the kingdoms of life. Macromolecular binding and folding reactions critical to unique biological functions are generally referred to as 'reversible associations'. Among the techniques that have been developed for the study of reversible associations, footprinting occupies a unique niche. Unlike structural methods such as x-ray crystallography and nuclear magnetic resonance (NMR), footprinting achieves site-specific resolution without extensive infrastructure, makes parsimonious use of biological samples and can be performed at dilute concentrations of macromolecules. Footprinting can map static structures as well as equilibrium and time-dependent transitions. The single residue resolution of footprinting can be used to develop detailed models of macromolecular structure, map ligand binding sites and follow conformational changes (FIG. 1). Computational tools are being developed that utilize the ensemble of individual measurements of the residue solvent accessibility to generate structural models of proteins and nucleic acids [6-10].

Cleavage of RNA and DNA by hydroxyl radicals is relatively insensitive to base sequence and whether a nucleic acid is single or double stranded [11, 12]. That hydroxyl radical cleavage of nucleic acids is quantitatively correlated with the solvent accessibility of the phosphodiester backbone has been demonstrated through comparisons of hydroxyl radical footprints with solvent accessibility calculations from crystal structures for protein-DNA complexes [13, 14] and RNA tertiary structures [15-19]. Backbone cleavage of DNA by hydroxyl radical is correlates with the accessible surface of the hydrogen atoms of the nucleotide sugar [20]. Hydroxyl radical footprinting yields a robust and readily interpretable measure of the structure and interactions of nucleic acids (FIG. 1). The availability of modern analysis tools such as CAFA [1] strengthens the feasibility of this method.

Hydroxyl radical footprinting was first extended to proteins by monitoring cleavage of the peptide backbone by gel electrophoresis [21, 22]. However, peptide bond cleavage is inefficient [23]. Thus, further development of protein hydroxyl radical footprinting has focused on the oxidation of amino acid side chains (reviewed in [24] and [25, 26]). Mass spectrometric analysis of proteolytic fragments is used to quantitate the oxidation rate of individual or groups of amino acid side chains. The differential reactivity of the amino acid side chains to oxidation is addressed in thermodynamic and kinetic analyses by quantitating the relative change in residue reactivity [24, 27]. A relationship between hydroxyl radical reactivity and solvent accessibility is emerging for proteins (reviewed in [24] & [25, 26]).

An important virtue of footprinting is that it can provide solution structural information with single residue resolution coupled to thermodynamic and kinetic transitions. Quantitative protocols have been extensively used to determine thermodynamic [3] and kinetic [31-34] constants describing protein-DNA interactions (reviewed in [3]). These protocols have been successfully extended to multiple implementations of quantitative hydroxyl radical footprinting [35-37] (see below). Protocols for thermodynamic protein hydroxyl radical footprinting have been published [38]. The individual-site isotherms [39, 40] and kinetic progress curves [31, 32] determined from thermodynamic and kinetic footprinting studies, respectively, provide an ensemble of local measures of macromolecular transitions from which detailed energetic and mechanistic portraits can be painted [41-44].

Footprinting assays for DNA, RNA and proteins have been developed using a wide range of reagents including the hydroxyl radical (.OH). The hydroxyl radical is among the most reactive and promiscuous of chemical oxidants [45]. Hydroxyl radical can be generated in solution by the Fenton-Haber-Weiss reaction according to the reaction $$\text{Fe(II)-EDTA} + \text{H}_2\text{O}_2 \rightarrow \text{Fe(III)-EDTA} + .\text{OH} + \text{OH}^- \qquad (1).$$

Tullius and co-workers showed that a convenient implementation of this chemistry for footprinting is to reductively cycle Fe(III) back to Fe(II) by the addition of ascorbate [13, 46, 47],

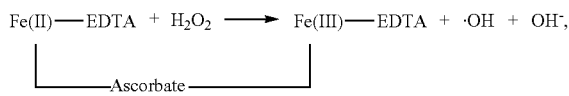

(2)

allowing low concentrations (µM) of the iron catalyst in the reaction mixture. This method is widely applied and inexpensive to perform. The reagent concentrations typically used in static and equilibrium .OH footprinting studies are µM in Fe(II)-EDTA and mM in $H_2O_2$ and ascorbate with reaction times of several to tens of minutes. Obviously, long reaction times are incompatible with high-throughput implementations.

A method using equation 1 where Fe(II) is stoichiometrically consumed by reaction with $H_2O_2$ to produce hydroxyl radicals on the millisecond timescale was recently developed [48-50]. While the reaction time is fast, impediments to high-throughput implementation of equation 1 include the need to precisely add high concentrations of the two reactants and auto oxidation of Fe(II).

Peroxonitrite has been used to hydroxyl radical footprint macromolecules [35, 51]. This reagent has not gained wide acceptance due to limitations on the solution conditions under which the reagent produces significant quantities of hydroxyl radical.

A recently developed method photolyzes $H_2O_2$ with UV radiation [25, 26, 52]. The use of UV radiation precludes this approach for DNA and RNA; nucleic acids are damaged by even limited exposure to short wavelength UV light. Thus, a disadvantage of $H_2O_2$ photolysis is that it is not general to both proteins and nucleic acids.

Radiolysis of water by ionizing radiation produced either from low flux gamma sources and high flux synchrotron beams has been effectively used to footprint DNA, RNA and proteins [16, 37, 53-56]. The advantage of radiolysis compared to the above described methods is that 'nothing but light' is added to the solutions containing the macromolecules to be footprinted. The disadvantage of low flux gamma sources is the need for an expensive gamma source, the long exposure required and cumbersome sample loading and unloading. While high flux synchrotron beams allow very short exposure times, substantial heat may be generated that is intolerable to biological samples. More importantly, the use of a synchrotron requires an application for beamtime and the transport of samples to a remote facility. Therefore, synchrotron footprinting is incompatible with laboratory-based high-throughput implementation.

The past decade has seen the advent of high-throughput structure determination initiatives focused on proteins, DNA and RNA. These initiatives are typically grouped under the rubric 'structural genomics'. High-throughput structure determination may be particularly valuable in screening studies where large numbers of structures and/or complexes need to be interrogated. Biological function may be revealed only by understanding the acquisition of structure as a function of time or the binding of a ligand requiring the determination of multiple structures for a single reaction.

High throughput structural initiatives have had limited to moderate success despite the infusion of many millions of dollars. While atomic resolution structures are the gold standard for structure determination, biological function can often be gleaned from lower resolution structures. In many cases, the complexity or size of macromolecules and complexes precludes determination of an atomic resolution structure. RNA molecules of even moderate size are notoriously refractory to structure determination.

SUMMARY OF THE INVENTION

The present inventors have discovered that a new use for a common and inexpensive persulfide, namely pyrite, which is capable of generating reactive oxygen species (ROS). Specifically, the ROS, including the hydroxyl radical, can be used in hydroxyl radical footprinting. In view of this discovery, the present inventors have designed solid state apparatuses for high-throughput structural mapping of proteins and nucleic acids which possess significant advantages over the currently available methods for structural mapping. Specifically, the present inventions are more cost effective, efficient, and do not introduce reagents into the solution containing the molecules of interest.

The present invention is directed to a apparatus for structural mapping of a macromolecule comprising an amount of persulfide effective to generate hydroxyl radicals upon contact with an aqueous solution.

The present invention is further directed to a method for structural mapping a macromolecule in an aqueous solution comprising (a) contacting the aqueous solution containing the macromolecule with a persulfide such that hydroxyl radicals are generated, (b) incubating the aqueous solution containing the macromolecule such that the macromolecule is (i) cleaved by the hydroxyl radicals, thereby producing cleaved macromolecule fragments or (ii) oxidized by the hydroxyl radicals, thereby producing macromolecules of altered molecular weight, and (c) analyzing the cleaved macromolecule fragments or macromolecules of altered molecular weight produced in step (b) via a structural genomics method, thereby structural mapping the macromolecule.

The present invention is further directed to a method for structural mapping a plurality of macromolecules in parallel, wherein each macromolecule is in a separate aqueous solution, comprising (a) contacting the aqueous solutions containing the macromolecules with separate persulfide-lined chambers such that hydroxyl radicals are generated, (b) incubating the aqueous solutions such that the macromolecules are (i) cleaved by the hydroxyl radical, thereby producing cleaved macromolecule fragments or (ii) oxidized by the hydroxyl radicals, thereby producing macromolecules of altered molecular weight, and (c) analyzing the cleaved macromolecule fragments or macromolecule of altered molecular weight produced in step (b) via a structural genomics method, thereby structural mapping the macromolecules.

DETAILED DESCRIPTION OF THE INVENTION

The present invention provides an apparatus for structural mapping of a macromolecule comprising an amount of persulfide effective to generate hydroxyl radicals upon contact with an aqueous solution.

A suitable apparatus for the present invention will comprise an amount of persulfide which is contactable by an aqueous solution containing the macromolecule to be structurally mapped. After contacting the macromolecule solution with the persulfide such that hydroxyl radicals are generated, the macromolecule solution is collected to be further analyzed. One skilled in the art would be able to envision and design numerous apparatuses which fit this criteria.

Persulfides refer to one compound of a series of sulfides that contains more atoms of sulfur than any other compound in the series. Persulfides can also refer to the sulfur analog of a peroxide. Examples of persulfides include, but are not limited to, pyrite, bravoite, caswellsilverite, cattierite, chalcopyrite, hauerite, molybdenite, and vaesite. In the preferred embodiment, the persulfide is pyrite. Preferably, the persulfide is in powder form.

Figure 3:
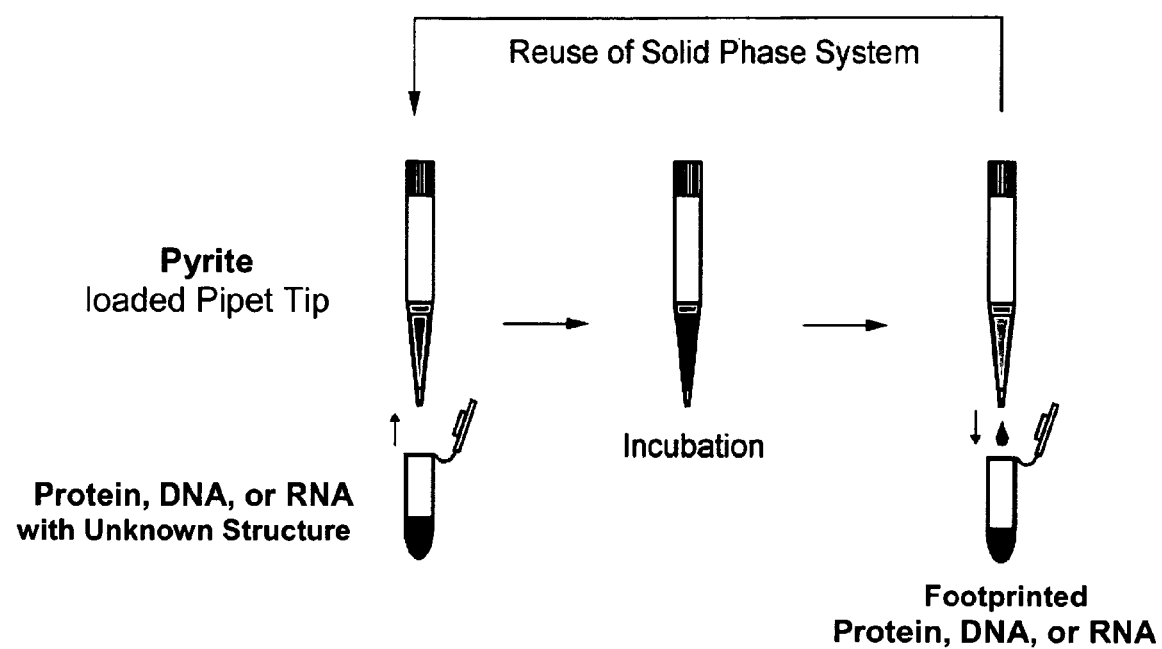
FIG. 3. Pipette pyrite cartridge for high-throughput footprinting.

In one embodiment of the present invention, the apparatus comprises a pipette tip. For example, the persulfide can be embedded between one or more porous discs in the pipette tip. In another example of the present invention, the persulfide can be embedded between two porous discs in the pipette disc. An example of this apparatus is illustrated in FIG. 3.

Figure 5:
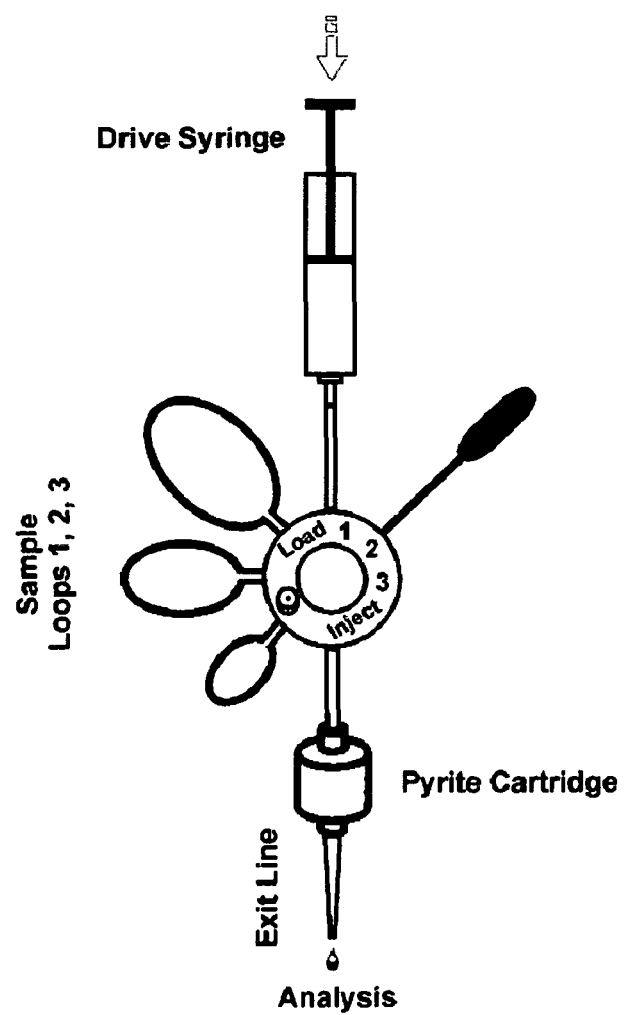
FIG. 5. Schematic representation of the column cartridge model for biopolymer footprinting.

In another embodiment of the present invention, the apparatus comprises a cartridge to be connected to a manual syringe. In this embodiment, the persulfide is located in the cartridge which is contacted with the macromolecule solution pushed through it via the manual syringe. An example of this apparatus is illustrated in FIG. 5. In another embodiment, the apparatus comprises a cartridge to be connected to an automated flow system, wherein the persulfide is contacted with the macromolecule solution via the automated flow system. One example of a suitable automated flow system is a high performance liquid chromatography-like injection system.

Figures 6A, 6B, 6C:
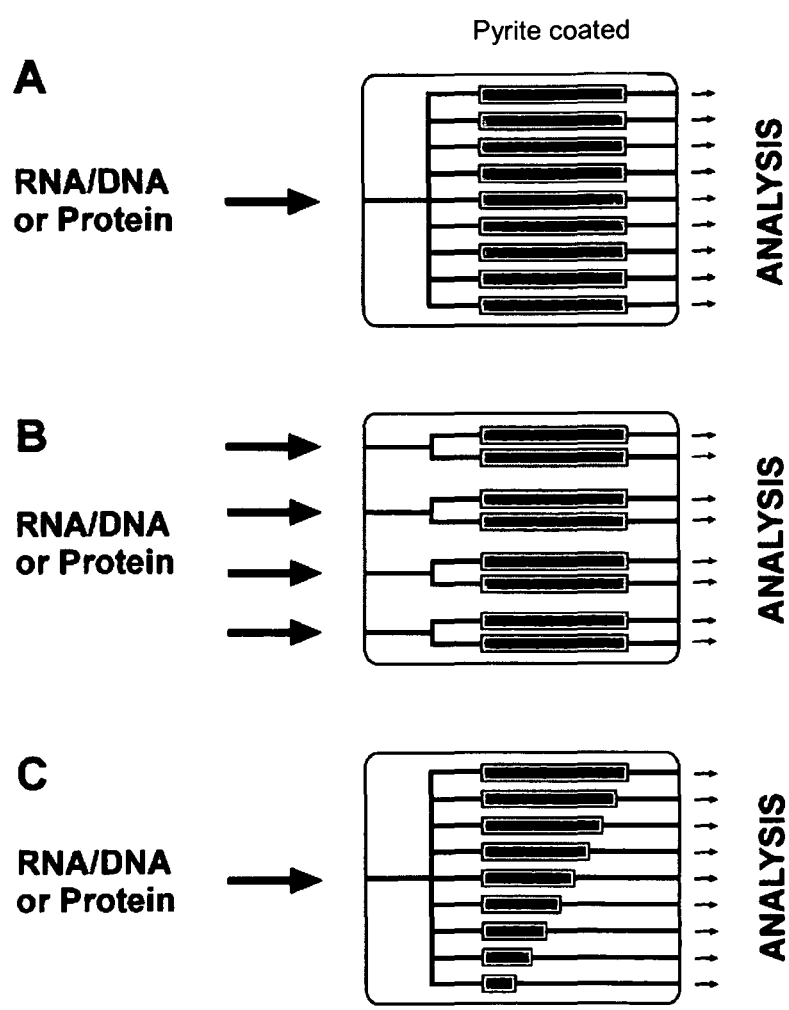
FIGS. 6A-6C. Three configurations for microfabricated solid-state generator footprinting chips.

In another embodiment of the present invention, the apparatus comprises a microfabricated mixing device. In one embodiment, the microfabricated mixing device comprises a microfabricated chip. In one embodiment, chip comprises one or more persulfide-lined chambers for the structural mapping of a single macromolecule. As illustrated in FIG. 6A, one example of the microfabricated chip comprises chambers of equal length. As illustrated in FIG. 6C, another example of the microfabricated chip comprises chambers of different lengths. By varying the lengths of the persulfide-lined chambers, one can control the duration of contact between the persulfide and the macromolecule solution.

In another embodiment of the present invention, the chip comprises two or more persulfide-lined chambers for the structural mapping of two or more macromolecules. In this embodiment, the two or more persulfide-lined chambers are separated from one another so as to avoid cross-contamination of the macromolecules to be structurally mapped. In one embodiment, the chambers are equal length. An example of such a microfabricated chip is illustrated in FIG. 6B. In other embodiments, the chambers are different lengths.

Due to the cost-effectiveness advantages of the present invention, the apparatus can be designed for one-time use, and therefore disposable. In another embodiment, the apparatus is reusable. An apparatus can be reusable if its design is such that the persulfide can be cleansed of prior macromolecule solutions.

The above-described apparatuses are useful for structural mapping of macromolecules. In one embodiment, the present invention provides a method for structural mapping a macromolecule in an aqueous solution comprising (a) contacting the aqueous solution containing the macromolecule with a persulfide such that hydroxyl radicals are generated, (b) incubating the aqueous solution containing the macromolecule such that the macromolecule is (i) cleaved by the hydroxyl radicals, thereby producing cleaved macromolecule fragments or (ii) oxidized by the hydroxyl radicals, thereby producing macromolecules of altered molecular weight, and (c) analyzing the cleaved macromolecule fragments or macromolecules of altered molecular weight produced in step (b) via a structural genomics method, thereby structural mapping the macromolecule.

A macromolecule which can be structural mapped by the above methods includes, but is not limited to, a protein, a DNA, an RNA, a protein-protein complex, a protein-DNA complex, a protein-RNA complex, or an RNA-DNA complex.

Numerous structural genomics methods are known in the art and can be used in the described methods for structural mapping. Examples of such methods include, but are not limited to, capillary automated sequencing analysis or mass spectrometry, such as matrix assisted laser desorption and ionization mass spectrometry.

The present invention also provides a method for structural mapping a plurality of macromolecules in parallel, wherein each macromolecule is in a separate aqueous solution, comprising (a) contacting the aqueous solutions containing the macromolecules with separate persulfide-lined chambers such that hydroxyl radicals are generated, (b) incubating the aqueous solutions such that the macromolecules are (i) cleaved by the hydroxyl radicals, thereby producing cleaved macromolecule fragments or (ii) oxidized by the hydroxyl radicals, thereby producing macromolecules of altered molecular weight, and (c) analyzing the cleaved macromolecule fragments or macromolecules of altered molecular weight produced in step (b) via a structural genomics method, thereby structural mapping the macromolecules. The various types of macromolecules which can be structurally mapped and structural genomics methods which can be used in this method are described above.

This invention will be better understood from the Examples, which follow. However, one skilled in the art will readily appreciate that the specific methods and results discussed are merely illustrative of the invention as described more fully in the claims that follow thereafter.

EXAMPLES

Figure 1:
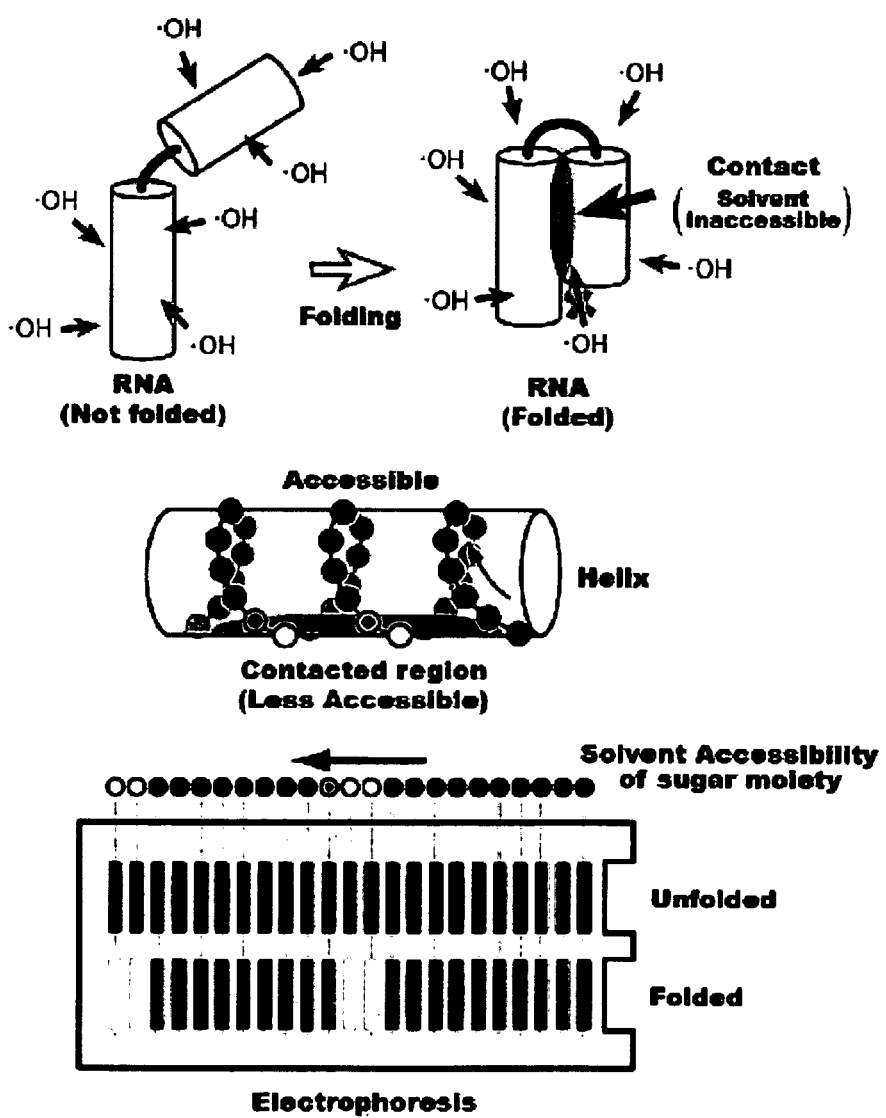
FIG. 1. Summary of the determination of local solvent inaccessible regions of RNA by hydroxyl radical footprinting.
Figure 2:
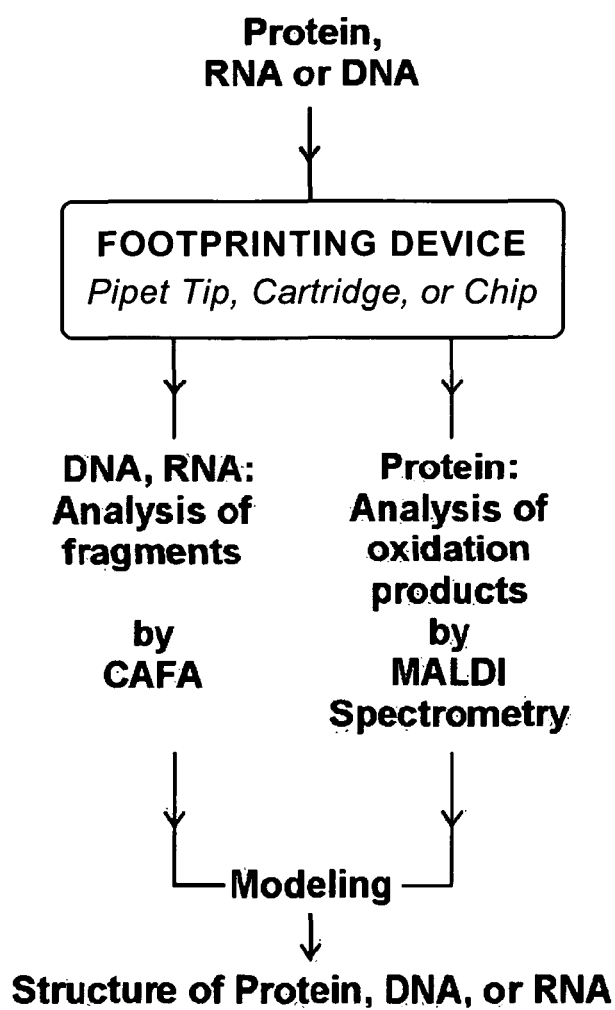
FIG. 2. Flow chart summarizing the determination of structural models by footprinting. Analysis of oxidation products of nucleic acids and proteins might occur by CAFA [1] and MALDI spectrometry [2], respectively.

FIG. 2 illustrates the strategy underlying the present invention. The apparatuses of the present invention address the first step in this process, the generation of hydroxyl radical for the controlled oxidation of the macromolecules. The ideal radical generator for high-throughput hydroxyl radical footprinting should fulfill the following criteria: 1) applicable to proteins and nucleic acids; 2) quantitative; 3) inexpensive to build; 4) inexpensive to use; 5) easy and reliable to use; and 6) do not require the addition of reagents to protein or nucleic acid containing solutions. The apparatuses described herein fulfill these criteria.

Three different embodiments of the present invention are described below: 1) a cartridge that will fit on the end of a pipette (FIG. 3) suitable for use with either hand pipetting or an autosampler/robotic system (FIG. 4), 2) a continuous flow cartridge that could be affixed to the end of a syringe and hand pumped or incorporated into a more elaborate flow system such as a pump driven manifold (FIG. 5), and 3) a microfabricated mixing device for use in 'lab-on-a-chip' instruments. It is envisioned the fabricated mixers be multi-channeled and thus capable of high throughput (FIG. 6). It should be noted that devices one and two can be adopted by laboratories with no infrastructure investment thereby providing an easy entry point of this novel technology that will facilitate its adoption. The matrix for our hydroxyl radical generators is inexpensive; the kilogram of pure crystalline pyrite used in the preliminary studies costs $42.00 (including shipping). Each prototype tip requires 0.223 grams of pyrite. Thus, the approximate material cost (tip, plugs and pyrite) of each prototype tip is 10¢.

Example 1

Figure 4:
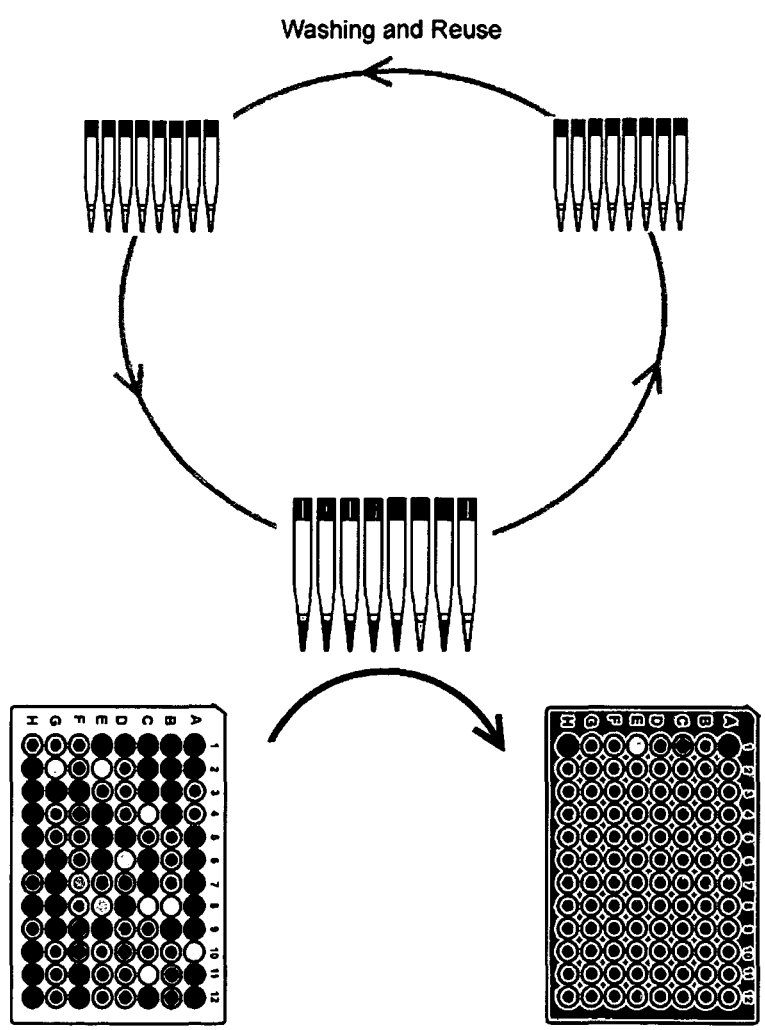
FIG. 4. Pipette pyrite cartridge implemented for high-throughput footprinting.

FIG. 3 shows the design of one embodiment of a pipette cartridge. It consists of a pipette tip and two porous disks (1) which embed powdered pyrite (2) of 20-200 μm. DNA, RNA, or protein solution can be drawn into the cartridge with a pipette, allowed to incubate and then expelled into a collection tube (shown) or directly into an appropriate analysis device. The pipette tip can be used with a multi-channel dispenser to perform high-throughput footprinting experiments (FIG. 4). In addition, the pyrite tips can be reused by incorporating a washing cycle in the experimental protocol. The number of usable cycles for this hydroxyl radical generator has not been determined.

FIG. 4 illustrates how the pyrite tip can be readily implemented in a moderate- and high-throughput screening protocols. Samples are loaded in a standard 96 well plate. One row of samples is drawn into a set of pyrite tips, incubated for the desired reaction tip and then dispensed into a second collection plate for additional processing (shown) or directly into an analytical instrument. The used tips could either be discarded or washed and reused as shown in the figure. Moderate-throughput is attained with a hand multi-channel pipettor. High-throughput footprinting is attainable using widely available robotic autosamplers that are designed to automatically carry out the sequence of events depicted in FIG. 4. Hundreds, if not thousands, of samples could be quickly, efficiently and inexpensively footprinted using pyrite tips in the scheme outlined in FIGS. 3 and 4.

Example 2

An alternative continuous flow design for the solid-state hydroxyl radical generator is shown in FIG. 5 that is suitable for use with a manual syringe or within an automated flow system (shown). It consists of a synthesis column (Glen research) with luer fittings and 0.2 μm frits at each end. The column is filled with powdered pyrite as described above. The cartridge is connected to a HPLC like injection system consisting of an injector with sample loops and a syringe pump. Upon filling of the sample loop and injection, the buffer of the drive syringe pushes the protein, DNA, or RNA solution into the pyrite cartridge whereat the degree of oxidation or cleavage of the biopolymer is determined by the speed of the buffer flow. After passing the exit line, the reaction solution is collected in a container or a corresponding analysis device. The footprinting cartridge can be readily implemented for high-throughput footprinting through a robotic system utilizing multiple cartridges, programmed drive syringes, sample loops and automated sample collection. As noted, an advantage of the tip and cartridge designs shown in FIGS. 3 and 5 is that they can be implemented without an investment in infrastructure and then be scaled up to high-throughput by purchase of the appropriate robotic devices.

Prophetic Example

However, the potential of high-throughput hydroxyl radical footprinting will be realized by incorporating our solid-state generator into microfabricated devices for use in lab-on-a-chip machines. Microfabrication allows virtually unlimited mixing and collecting configurations that can be tailored to particular experimental protocols.

FIG. 6 outlines three simple designs. In Panel A, a RNA, DNA or protein sample containing solution is drawn into the device, flows through a parallel array of pyrite-containing chambers and exit into separate collection vessels. This configuration allows the rapid acquisition of experimental replicates. Panel B outlines a configuration in which multiple samples are footprinted in parallel. The footprinting reaction time is controlled by the flow rate in these configurations. Panel C diagrams a configuration in which a single sample is partitioned among channels containing solid-state generators of increasing length. The degree of biopolymer oxidation will depend on the length of the pyrite containing channel area. This design automatically collects a 'dose-response' set of samples in which the footprinting reaction time is systematically increased. Such dose-response data is particular important to the study of proteins by footprinting and is valuable to the development and testing of structural models of both proteins and nucleic acids.

It should be noted that among the virtues of microfabrication is design flexibility. For example, the configurations shown in panels A, B and C could be combined to produce a chip that processes replicates of multiple samples oxidized by a series of discrete amounts. It is envisioned that laboratories would determine the utility of the present invention using the simple generators shown in FIGS. 3 and 5, and then progress to microfabricated chips as the utility of the method is demonstrated and high-throughput is desired. If a standard platform is used, many laboratories could utilize a shared analyzer by purchasing either standard or custom configured chips.

REFERENCES

1. Mitra, S., I. Shcherbakova, R. B. Altman, M. Brenowitz, & A. Laederach, *High-throughput single-nucleotide structural mapping by Capillary Automated Footprinting Analysis*. Nucleic Acids Res, 2008. 36(11):e63, epub May 13, 2008.
2. Gupta, S., et al., *DNA and protein footprinting analysis of the modulation of DNA binding by the N-terminal domain of the Saccharomyces cerevisiae TATA Binding Protein*. 2007: 46(35):9886-9898, epub Aug. 7, 2007.
3. Petri, V. & M. Brenowitz, *Quantitative nucleic acids footprinting: thermodynamic and kinetic approaches*. Curr Opin Biotechnol, 1997. 8(1): p. 36-44.
4. Tullius, T. D., *Physical studies of protein-DNA complexes by footprinting*. Annu Rev Biophys Biophys Chem, 1989. 18: p. 213-37.
5. Brenowitz, M., D. F. Senear, M. A. Shea, & G. K. Ackers, *Quantitative DNase footprint titration: a method for studying protein-DNA interactions*. Methods Enzymol, 1986. 130: p. 132-81.
6. Greenbaum, J. A., S. C. Parker, & T. D. Tullius, *Detection of DNA structural motifs in functional genomic elements*. Genome Res, 2007. 17(6): p. 940-6.

7. Greenbaum, J. A., B. Pang, & T. D. Tullius, *Construction of a genome-scale structural map at single-nucleotide resolution.* Genome Res, 2007. 17(6): p. 947-53.
8. Birney, E., et al., *Identification and analysis of functional elements in 1% of the human genome by the ENCODE pilot project.* Nature, 2007. 447(7146): p. 799-816.
9. Kamal, J. K., S. A. Benchaar, K. Takamoto, E. Reisler, & M. R. Chance, *Three-dimensional structure of cofilin bound to monomeric actin derived by structural mass spectrometry data.* Proc Natl Acad Sci USA, 2007. 104(19): p. 7910-5.
10. Takamoto, K., J. K. Kamal, & M. R. Chance, *Biochemical implications of a three-dimensional model of monomeric actin bound to magnesium-chelated ATP.* Structure, 2007. 15(1): p. 39-51.
11. Latham, J. A. & T. R. Cech, *Defining the inside and outside of a catalytic RNA molecule.* Science, 1989. 245 (4915): p. 276-82.
12. Celander, D. W. & T. R. Cech, *Iron(II)-ethylenediaminetetraacetic acid catalyzed cleavage of RNA and DNA oligonucleotides: similar reactivity toward single-and double-stranded forms.* Biochemistry, 1990. 29(6): p. 1355-61.
13. Dixon, W. J., et al., *Hydroxyl radical footprinting.* Methods Enzymol, 1991. 208: p. 380-413.
14. Pastor, N., H. Weinstein, E. Jamison, & M. Brenowitz, *A Detailed Interpretation of OH Radical Footprints in a TBP-DNA Complex Reveals the Role of Dynamics in the Mechanism of Sequence-specific Binding.* J Mol Biol, 2000. 304(1): p. 55-68.
15. Cate, J. H., et al., *Crystal structure of a group I ribozyme domain: principles of RNA packing [see comments].* Science, 1996. 273(5282): p. 1678-85.
16. Sclavi, B., S. Woodson, M. Sullivan, M. R. Chance, & M. Brenowitz, *Time-resolved synchrotron X-ray "footprinting", a new approach to the study of nucleic acid structure and function: application to protein-DNA interactions and RNA folding.* J Mol Biol, 1997. 266(1): p. 144-59.
17. Celander, D. W. & T. R. Cech, *Visualizing the higher order folding of a catalytic RNA molecule.* Science, 1991. 251 (4992): p. 401-7.
18. Lehnert, V., L. Jaeger, F. Michel, & E. Westhof, *New loop-loop tertiary interactions in self-splicing introns of subgroup IC and ID: a complete 3D model of the Tetrahymena thermophila ribozyme.* Chem Biol, 1996. 3(12): p. 993-1009.
19. Golden, B. L., A. R. Gooding, E. R. Podell, & T. R. Cech, *A preorganized active site in the crystal structure of the Tetrahymena ribozyme [see comments].* Science, 1998. 282(5387): p. 259-64.
20. Balasubramanian, B., W. K. Pogozelski, & T. D. Tullius, *DNA strand breaking by the hydroxyl radical is governed by the accessible surface areas of the hydrogen atoms of the DNA backbone.* Proc Natl Acad Sci USA, 1998. 95(17): p. 9738-43.
21. Heyduk, E. & T. Heyduk, *Mapping protein domains involved in macromolecular interactions: a novel protein footprinting approach [published erratum appears in Biochemistry 1995 Nov. 21; 34(46):15388].* Biochemistry, 1994. 33(32): p. 9643-50.
22. Zhong, M., L. Lin, & N. R. Kallenbach, *A method for probing the topography and interactions of proteins: footprinting of myoglobin.* Proc Natl Acad Sci USA, 1995. 92(6): p. 2111-5.
23. King, P. A., et al., *A stable solid that generates hydroxyl radical upon dissolution in aqueous solution. Reaction with proteins and nucleic acid.* J Am Chem Soc, 1992. 114: p. 5430-5432.
24. Guan, J. Q. & M. R. Chance, *Structural proteomics of macromolecular assemblies using oxidative footprinting and mass spectrometry.* Trends Biochem Sci, 2005. 30(10): p. 583-92.
25. Hambly, D. M. & M. L. Gross, *Laser flash photolysis of hydrogen peroxide to oxidize protein solvent-accessible residues on the microsecond timescale.* J Am Soc Mass Spectrom, 2005. 16(12): p. 2057-63.
26. Aye, T. T., T. Y. Low, & S. K. Sze, *Nanosecond laser-induced photochemical oxidation method for protein surface mapping with mass spectrometry.* Anal Chem, 2005. 77(18): p. 5814-22.
27. Maleknia, S. D., M. Brenowitz, & M. R. Chance, *Millisecond radiolytic modification of peptides by synchrotron X-rays identified by mass spectrometry.* Anal Chem, 1999. 71(18): p. 3965-73.
28. Brenowitz, M. & D. F. Senear, *DNase I Footprint Analysis of Protein-DNA Binding,* in *Current Protocols in Molecular Biology,* F. M. Ausubel, et al., Editors. 1989, John Wiley and Sons: New York. p. Unit 12.4.
29. Koblan, K. S., D. L. Bain, D. Beckett, M. A. Shea, & G. K. Ackers, *Analysis of site-specific interaction parameters in protein-DNA complexes.* Methods Enzymol, 1992. 210: p. 405-25.
30. Senear, D. F. & D. W. Bolen, *Simultaneous analysis for testing of models and parameter estimation.* Methods Enzymol, 1992. 210: p. 463-81.
31. Hsieh, M. & M. Brenowitz, *Comparison of the DNA association kinetics of the Lac repressor tetramer, its dimeric mutant Lacladi, and the native dimeric Gal repressor.* J Biol Chem, 1997. 272(35): p. 22092-6.
32. Hsieh, M. & M. Brenowitz, *Quantitative kinetics footprinting of protein-DNA association reactions.* Methods Enzymol, 1996. 274: p. 478-92.
33. Mollah, A. K. M. M. & M. Brenowitz, *Quantitative DNase I Kinetics Footprinting,* in *Protein-DNA Interactions—a Practical Approach,* A. Travers and M. Buckle, Editors. 2000, IRL Press at Oxford University Press: Oxford.
34. Petri, V., M. Hsieh, & M. Brenowitz, *Thermodynamic and kinetic characterization of the binding of the TATA binding protein to the adenovirus E4 promoter.* Biochemistry, 1995. 34(31): p. 9977-84.
35. King, P. A., E. Jamison, D. Strahs, V. E. Anderson, & M. Brenowitz, *'Footprinting' proteins on DNA with peroxonitrous acid.* Nucleic Acids Res, 1993. 21(10): p. 2473-8.
36. Strahs, D. & M. Brenowitz, *DNA conformational changes associated with the cooperative binding of cl-repressor of bacteriophage lambda to OR.* J Mol Biol, 1994. 244(5): p. 494-510.
37. Sclavi, B., M. Sullivan, M. R. Chance, M. Brenowitz, & S. A. Woodson, *RNA folding at millisecond intervals by synchrotron hydroxyl radical footprinting.* Science, 1998. 279 (5358): p. 1940-3.
38. Kiselar, J. G., P. A. Janmey, S. C. Almo, & M. R. Chance, *Visualizing the Ca2+-dependent activation of gelsolin by using synchrotron footprinting.* Proc Natl Acad Sci USA, 2003. 100(7): p. 3942-7.
39. Ackers, G. K., A. D. Johnson, & M. A. Shea, *Quantitative model for gene regulation by lambda phage repressor.* Proc Natl Acad Sci USA, 1982. 79(4): p. 1129-33.
40. Ackers, G. K., M. A. Shea, & F. R. Smith, *Free energy coupling within macromolecules. The chemical work of* ligand binding at the individual sites in co-operative systems. J Mol Biol, 1983. 170(1): p. 223-42.
41. Shadle, S. E., et al., *Quantitative analysis of electrophoresis data: novel curve fitting methodology and its application to the determination of a protein-DNA binding constant.* Nucleic Acids Res, 1997. 25(4): p. 850-60.
42. Takamoto, K., Q. He, S. Morris, M. R. Chance, & M. Brenowitz, *Monovalent cations mediate formation of native tertiary structure of the Tetrahymena thermophila ribozyme.* Nat Struct Biol, 2002. 9(12): p. 928-933.
43. Takamoto, K., M. R. Chance, & M. Brenowitz, *Semi-automated, single-band peak-fitting analysis of hydroxyl radical nucleic acid footprint autoradiograms for the quantitative analysis of transitions.* Nucleic Acids Res, 2004. 32(15): p. E119.
44. Das, R., A. Laederach, S. M. Perlman, D. Herschlag, & R. B. Altman, *SAFA: Semi-Automated Footprinting Analysis software for high-throughput quantification of nucleic acid footprinting experiments.* RNA, 2005. 11(3): p. 344-54.
45. Buxton, G., C. Greenstock, W. Heiman, & A. Ross, *Critical review of rate constants for reactions of hydrated electrons, hydrogen atoms and hydroxyl radicals in aqueous solution.* J. Phys. Chem. Ref. Data., 2002. 17: p. 513-886.
46. Tullius, T. D. & B. A. Dombroski, *Hydroxyl radical "footprinting": high-resolution information about DNA-protein contacts and application to lambda repressor and Cro protein.* Proc Natl Acad Sci USA, 1986. 83(15): p. 5469-73.
47. Tullius, T. D. & J. A. Greenbaum, *Mapping nucleic acid structure by hydroxyl radical cleavage.* Curr Opin Chem Biol, 2005. 9(2): p. 127-34.
48. Shcherbakova, I. & M. Brenowitz, *Monitoring structural changes in nucleic acids with single residue spatial and millisecond time resolution by quantitative hydroxyl radical footprinting.* Nat Protoc, 2008. 3(2): p. 288-302.
49. Shcherbakova, I., S. Mitra, R. H. Beer, & M. Brenowitz, *Following molecular transitions with single residue spatial and millisecond time resolution.* Methods Cell Biol, 2008. 84: p. 589-615.
50. Shcherbakova, I., S. Mitra, R. H. Beer, & M. Brenowitz, *Fast Fenton footprinting: a laboratory-based method for the time-resolved analysis of DNA, RNA and proteins.* Nucleic Acids Res, 2006. 34(6): p. e48.
51. Chaulk, S. G. & A. M. MacMillan, *Characterization of the Tetrahymena ribozyme folding pathway using the kinetic footprinting reagent peroxynitrous acid.* Biochemistry, 2000. 39(1): p. 2-8.
52. Sharp, J. S., J. M. Becker, & R. L. Hettich, *Analysis of protein solvent accessible surfaces by photochemical oxidation and mass spectrometry.* Anal Chem, 2004. 76(3): p. 672-83.
53. Hayes, J. J., L. Kam, & T. D. Tullius, *Footprinting protein-DNA complexes with gamma-rays.* Methods Enzymol, 1990. 186: p. 545-9.
54. Ottinger, L. M. & T. D. Tullius, *High-Resolution in Vivo Footprinting of a Protein-DNA Complex Using Gamma Radiation.* J. Am. Chem. Soc., 2000. 122: p. 5901-5902.
55. Sclavi, B., S. Woodson, M. Sullivan, M. Chance, & M. Brenowitz, *Following the folding of RNA with time-resolved synchrotron X-ray footprinting.* Methods Enzymol, 1998. 295: p. 379-402.
56. Franchet-Beuzit, J., M. Spotheim-Maurizot, R. Sabattier, B. Blazy-Baudras, & M. Charlier, *Radiolytic footprinting. Beta rays, gamma photons, and fast neutrons probe DNA-protein interactions.* Biochemistry, 1993. 32(8): p. 2104-10.
57. Cohn, C., M. Borda, & M. Schroonen, *RNA decomposition by pyrite-induced radicals and possible role of lipids during the emergence of life.* Earth and Planetary Science Letters, 2004. 225: p. 271-278.
58. Schoonen, M., A. Smirnov, & C. Cohn, *A perspective on the role of minerals in prebiotic synthesis.* Ambio, 2004. 33(8): p. 539-51.
59. Cohn, C. A., et al., *Pyrite-induced hydroxyl radical formation and its effect on nucleic acids.* Geochem Trans, 2006. 7: p. 3.
60. Cohn, C. A., R. Laffers, S. R. Simon, T. O'Riordan, & M. A. Schoonen, *Role of pyrite in formation of hydroxyl radicals in coal: possible implications for human health.* Part Fibre Toxicol, 2006. 3: p. 16.
61. Cohn, C. A., R. Laffers, & M. A. Schoonen, *Using yeast RNA as a probe for generation of hydroxyl radicals by earth materials.* Environ Sci Technol, 2006. 40(8): p. 2838-43.

What is claimed is:

1. A method for structural mapping a macromolecule in an aqueous solution comprising: (a) contacting the aqueous solution containing the macromolecule with a persulfide of a persulfide-lined chamber such that hydroxyl radicals are generated; (b) incubating the aqueous solution containing the macromolecule such that the macromolecule is (i) cleaved by the hydroxyl radicals, thereby producing cleaved macromolecule fragments or (ii) oxidized by the hydroxyl radicals, thereby producing macromolecules of altered molecular weight; and (c) analyzing the cleaved macromolecule fragments or macromolecules of altered molecular weight produced in step (b) via a structural genomics method, thereby structural mapping the macromolecule.

2. The method of claim 1, wherein the macromolecule is a protein, a DNA, an RNA, a protein-protein complex, a protein-DNA complex, a protein-RNA complex, or an RNA-DNA complex.

3. The method of claim 1, wherein the structural genomics method is capillary automated sequencing analysis or mass spectrometry.

4. The method of claim 3, wherein the mass spectrometry is matrix assisted laser desorption and ionization mass spectrometry.

5. The method of claim 1, wherein the persulfide is contained in an apparatus for structural mapping of a macromolecule comprising an amount of persulfide effective to generate hydroxyl radicals upon contact with an aqueous solution.

6. The method of claim 1, further comprising structural mapping a plurality of macromolecules in parallel, wherein each macromolecule is in a separate aqueous solution, wherein step (a) comprises contacting each of the plurality of the aqueous solutions with separate persulfide-lined chambers such that hydroxyl radicals are generated.

7. The method of claim 1, wherein the persulfide-lined chambers are contained in an apparatus for structural mapping of a macromolecule comprising an amount of persulfide effective to generate hydroxyl radicals upon contact with an aqueous solution, wherein the apparatus comprises a microfabricated mixing device, wherein the microfabricated mixing device comprises a microfabricated chip, wherein the microfabricated chip comprises two or more persulfide-lined chambers for the structural mapping of two or more macromolecules.

* * * * *